United States Patent
Green

(10) Patent No.: US 6,685,677 B2
(45) Date of Patent: Feb. 3, 2004

(54) NEEDLE SHIELD CONVERTING TO A NEEDLELESS NEEDLE

(76) Inventor: Christopher H. Green, 801 Three Islands Blvd., Unit 211, Hallandale, FL (US) 33009

(*) Notice: Subject to any disclaimer, the term of this patent is extended or adjusted under 35 U.S.C. 154(b) by 0 days.

(21) Appl. No.: 09/924,244

(22) Filed: Aug. 7, 2001

(65) Prior Publication Data

US 2002/0019611 A1 Feb. 14, 2002

Related U.S. Application Data

(60) Provisional application No. 60/231,175, filed on Sep. 7, 2000.

(51) Int. Cl.[7] .................................................. A61M 5/32
(52) U.S. Cl. ...................................................... 604/198
(58) Field of Search ................................. 604/110, 192, 604/198, 263, 164.08, 165.03, 272; 128/919

(56) References Cited

U.S. PATENT DOCUMENTS

| 4,888,001 A | * | 12/1989 | Schoenberg | ................ 604/263 |
| 4,935,013 A | | 6/1990 | Haber et al. | |
| 4,950,250 A | * | 8/1990 | Haber et al. | ................ 604/198 |
| 5,304,137 A | * | 4/1994 | Fluke | ........................ 604/110 |
| 5,348,544 A | | 9/1994 | Sweeney et al. | |
| 5,531,713 A | | 7/1996 | Mastronardi et al. | |
| 5,704,919 A | | 1/1998 | Kraus et al. | |
| 5,713,872 A | | 2/1998 | Feuerborn et al. | |
| 5,755,696 A | * | 5/1998 | Caizza | ........................ 604/164 |
| 5,925,020 A | | 7/1999 | Nestell | |
| 5,951,525 A | | 9/1999 | Thorne et al. | |
| 5,993,418 A | | 11/1999 | Alexander | |
| 6,015,396 A | | 1/2000 | Buttgen et al. | |
| 6,126,641 A | | 10/2000 | Shields | |

* cited by examiner

Primary Examiner—Manuel Mendez
(74) Attorney, Agent, or Firm—Clifford W. Browning; Woodard, Emhardt, Moriarty, McNett & Henry LLP

(57) ABSTRACT

A needle assembly withdraws medicine from a vial having a rubber septum and injects the medicine into a port in a patient while not endangering the caregiver with an accidental stick with a contaminated used needle. The needle assembly includes a sharp hollow needle for penetrating a septum of a vial and a blunt cannula for injecting into an injection port. The needle can be of any type including intramuscular. The blunt cannula concentrically surrounding the sharp hollow needle, forms a liquid-tight seal with the sharp hollow needle, and extends relative to the sharp hollow needle in a locked position.

18 Claims, 5 Drawing Sheets

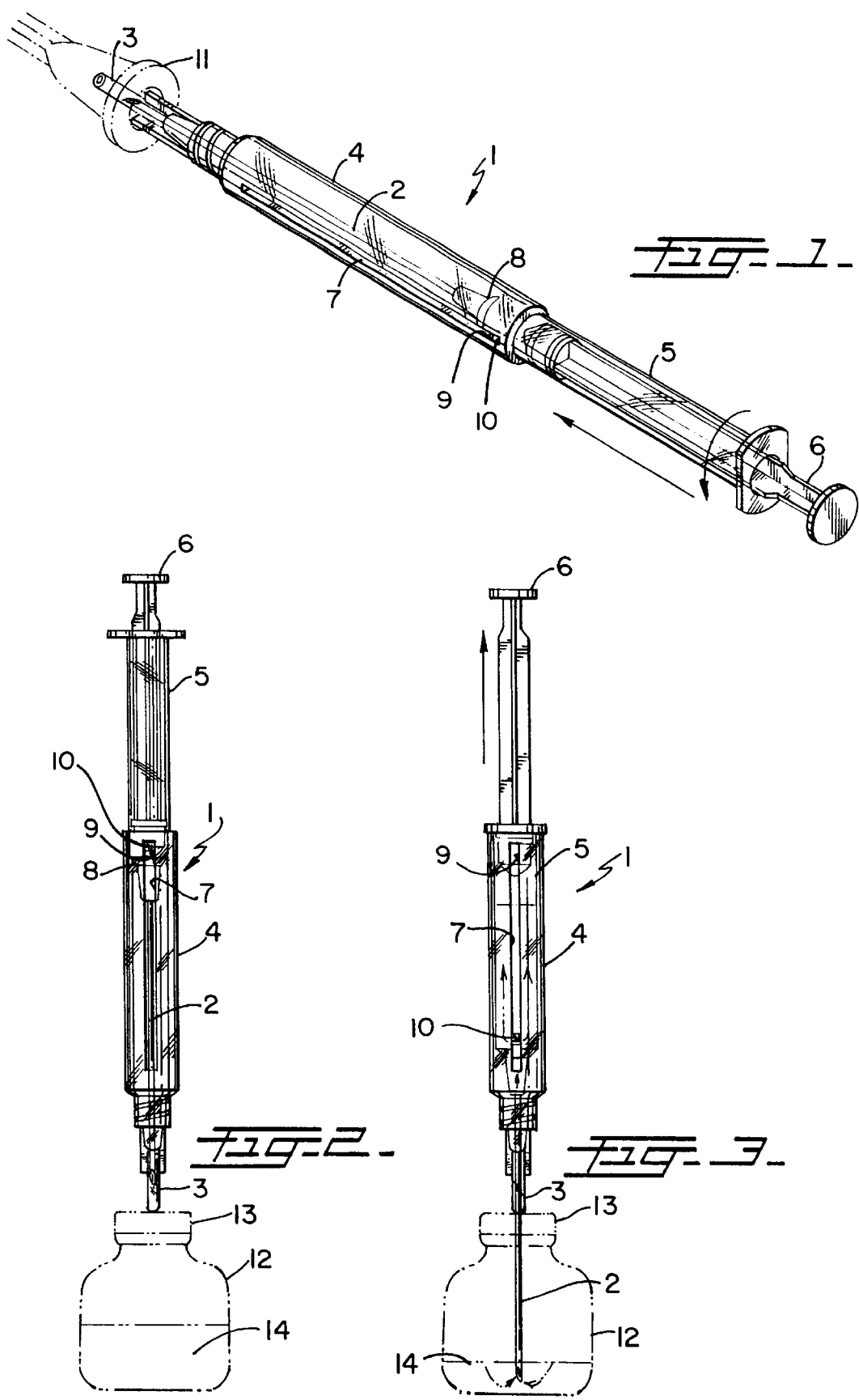

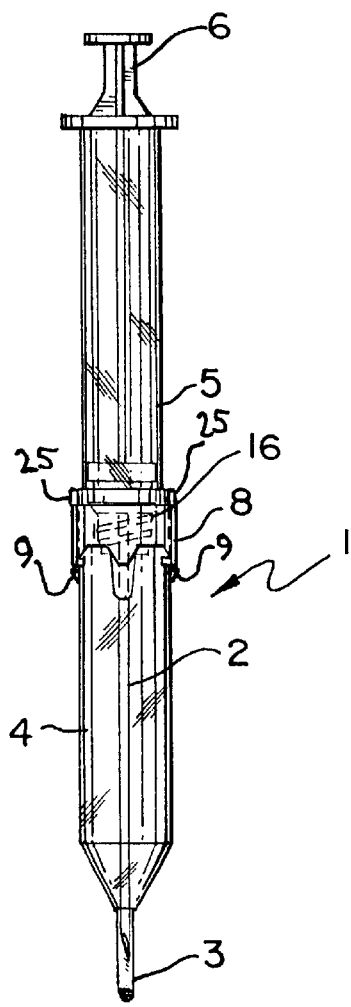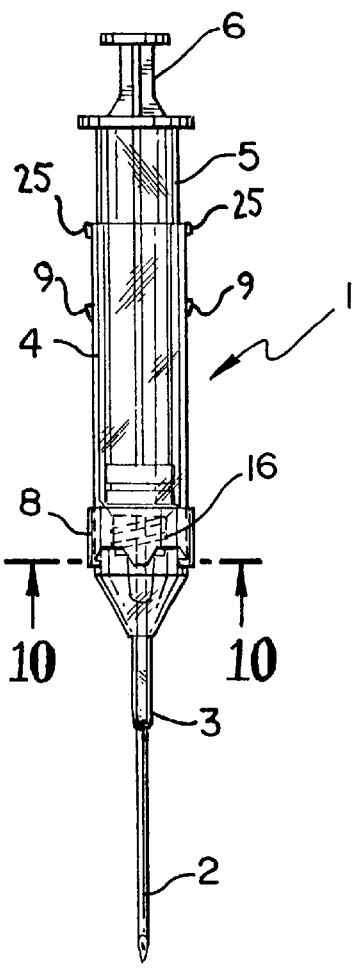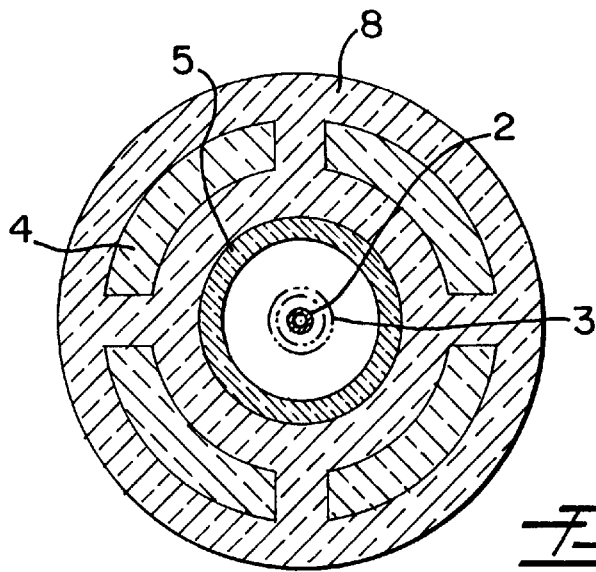

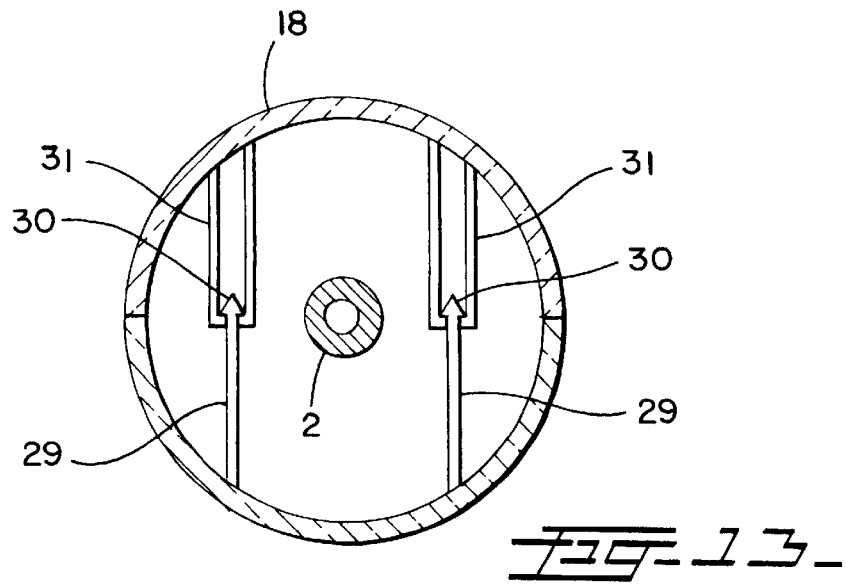
FIG-13-
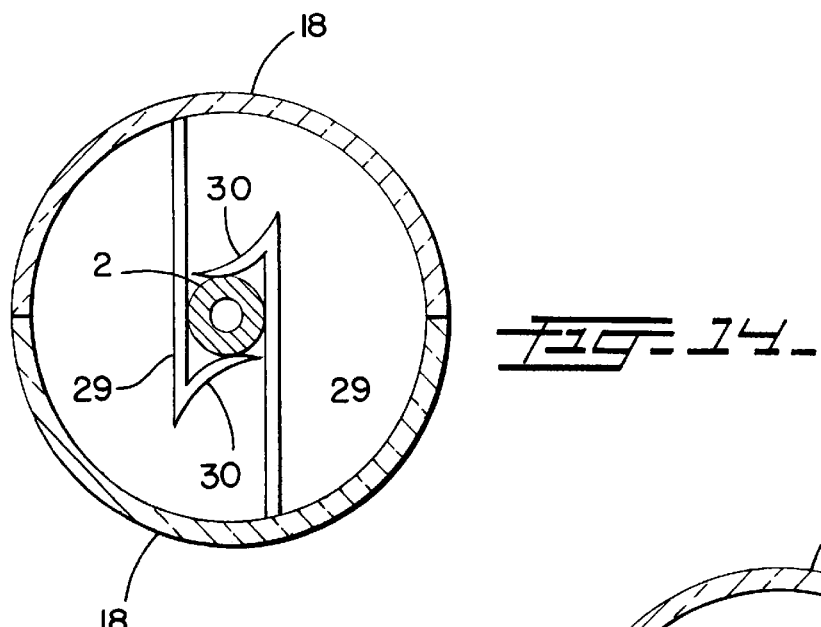
FIG-14-
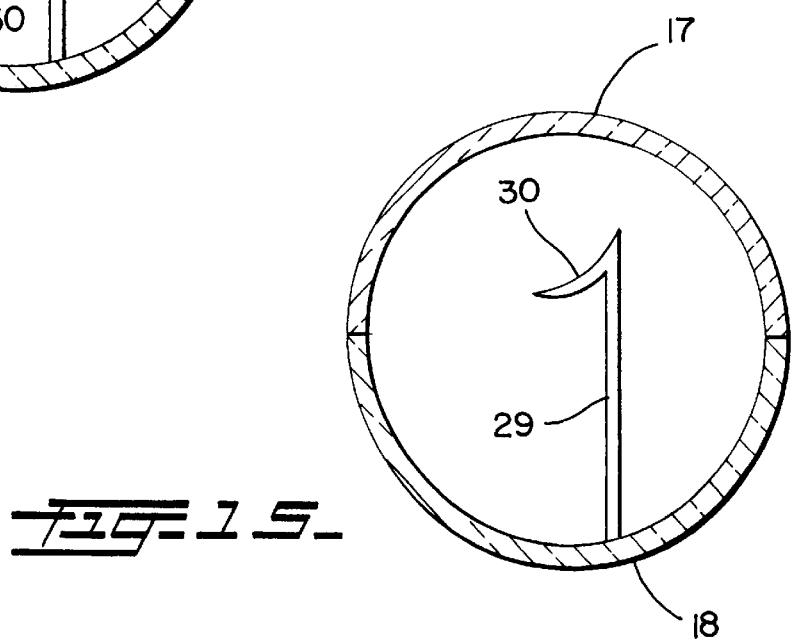
FIG-15-

ND# NEEDLE SHIELD CONVERTING TO A NEEDLELESS NEEDLE

CROSS-REFERENCE TO RELATED APPLICATION

This application claims the benefit of U.S. Provisional Application Ser. No. 60/231,175, filed Sep. 7, 2000.

BACKGROUND OF THE INVENTION

1. Field of the Invention

The invention relates to a needle assembly capable of withdrawing medicine from a vial, injecting into a port in a patient, and preventing accidental punctures or "sticks" from a contaminated needle. In particular, the invention relates to a needle assembly including a sharp hollow needle for penetrating a septum of a vial. The needle assembly also includes a blunt cannula for injecting into an injection port. The blunt cannula concentrically surrounds the sharp hollow needle, forms a liquid-tight seal with the cannula, and retractably extends relative to the sharp hollow needle.

2. Description of the Related Art

The spread of contagious blood-born diseases such as HIV and Hepatitis has provided incentive for many to invent syringes with safety devices to prevent people from accidentally sticking themselves or others with contaminated needles. These safety syringes have not become accepted because they are too difficult to use or too expensive.

As stated, many needle safety shield devices have been devised to reduce the risk of inadvertent needle punctures. Many of these devices are designed to slide over a used needle to a position where the needle is completely encased permanently so that an inadvertent needle puncture would be eliminated.

There are also needles called "Needleless needles" or "blunt plastic cannulas" that are needle substitutes. These blunt plastic cannulas are similar to needles in shape but are plastic and have a blunt end. They are only able to gain access into the body by way of a pre-slit injection port connected to a catheter. The injection port is designed specifically for receiving blunt plastic cannulas. These blunt plastic cannulas have a tremendous advantage over the conventional steel needles. Once the blunt plastic cannula is locked in place on the syringe, the fear of a possible contaminated needle stick is eliminated; the blunt plastic cannula cannot pierce the skin and only can gain access into the body through the pre-slit injection recepticle.

However, blunt plastic cannulas cannot pierce the rubber septums used to seal medicine vials. Therefore, a syringe having only a plastic blunt cannula cannot withdraw medicine from a vial through a rubber septum.

Another problem with some of the Needle safety shield devices (where the needle is permanently encased by an outer connecting structure) is that although the user can shield a used contaminate needle, a moment still exists where the sharp used needle is exposed. In this moment, a contaminated needle puncture can occur. Furthermore, the moment when the syringe is first removed is the most dangerous moment for accidental needle sticks caused by an uncooperative or convulsing patient.

Syringes with exchangeable blunt cannulas and sharp needles exist. A clean sharp needle is initially attached to a syringe. The sharp needle can pierce the rubber septum of a medicine vial for withdrawal of the medicine. Once filled, the still uncontaminated sharp needle is removed and a blunt plastic cannula is screwed onto the syringe. The patient is injected with the syringe and blunt cannula by using a pre-slit injection port. The now contaminated blunt plastic cannula is unable to pierce the caregiver's skin.

Although, the syringe with exchangeable tips appears to provide a solution, in practice, most health care workers have chosen not to use these syringes because they are too time consuming to use. When a nurse withdraws an intravenous solution from a vial, which must be accessed by a steel needle, rarely will the nurse, who is pushed for time, stop and change the steel needle and find a blunt plastic cannula with which to replace it. Again, this makes a contaminated needle strike possible.

Buttgen et al. (U.S. Pat. No. 6,015,396) disclose an Automatic Cannula Withdrawing Device for Injection Syringes. The syringe withdraws into a housing as the injection is completed. The housing shields the used needle and prevents unintended sticks. The housing does not form a cannula that can inject into a septum. Furthermore, if the volume held in the syringe is not fully injected, the needle is not retracted and unintentional sticks can occur.

Alexander (U.S. Pat. No. 5,993,418) discloses a Safety Syringe. In Alexander, the syringe includes a needle surrounded by fluid-tight barrel. The needle extends beyond the barrel and allows the needle to penetrate a vial and the skin of a patient. When the plunger is fully compressed, a lever causes the needle to retract within the barrel. The barrel of the safety syringe is not a cannula that can allow injections through pre-slit injection port. If the plunger is not fully compressed, the needle does not withdraw into the barrel. So, a used needle still can stick an injector.

Caizza (U.S. Pat. No. 5,755,696) discloses a Syringe Filling and Delivery Device. The syringe includes a needle and a coaxial cannula surrounding the needle. Springs urge the needle within the cannula. Pressing harder than the springs to extend the needle through the septum fills the syringe. During injection the cannula penetrates a rubber septum without extending the needle. No lock is included in Caizza. So, under enough force, such as an accident, a used needle can extend beyond the cannula and stick the injector.

Kraus et al. (U.S. Pat. No. 5,704,919) disclose an Intravenous Cannula Assembly. The assembly is for inserting a catheter intravenously. Once inserted, fluids can be injected or withdrawn through the assembly. The assembly includes a coaxial needle and cannula. Initially, the needle extends longer than the cannula. The extended needle pierces a patient's skin and vein. The needle is then withdrawn into a telescoping sleeve for disposal leaving a connected cannula. Separate tubing is then connected to the cannula. The Assembly is not a syringe. Because the needle is removed from the back of the assembly (where the volume of liquid to be injected would be in a syringe), the device cannot be adapted to a syringe.

Haber et al. (U.S. Pat. No. 4,950,250) disclose a Collapsible Needle Cover. The cover folds to expose a needle. The needle is exposed during injection and withdrawal of fluid from a vial. The unfolded cover prevents unintended sticks when extended. The cover is not able to act as a cannula through which injections take place.

SUMMARY OF THE INVENTION

It is accordingly an object of the invention to provide a needle assembly capable of withdrawing medicine from a vial having a rubber septum and injecting the medicine into a port in a patient while not endangering the care giver with an accidental stick with a contaminated used needle.

With the foregoing and other objects in view there is provided, in accordance with the invention, a needle assembly. The needle assembly includes a sharp hollow needle for penetrating a septum of a vial. The needle assembly also includes a blunt cannula for injecting into an injection port. The blunt cannula concentrically surrounds the sharp hollow needle and forms a liquid-tight seal with the needle. The blunt cannula retractably extends relative to the sharp hollow needle. By extending beyond the needle, the blunt cannula can be used to inject medicine into a port in a patient. However, this blunt cannula acts as a shield over the sharp needle, so, once the blunt cannula has been deployed, the sharp needle cannot penetrate a caregiver's skin.

In accordance with a further feature of the invention, the needle assembly includes a syringe connected longitudinally to the blunt cannula.

In accordance with a further feature of the invention, the needle assembly includes a wing having an upper wing element and a lower wing element joined by a hinge. The wing is fixed proximally to the sharp hollow needle and unfolds at the hinge to extend the blunt cannula beyond said sharp hollow needle.

In accordance with a further feature of the invention, the wing includes a lock preventing the wing from unfolding once the wing has been unfolded.

In accordance with a further feature of the invention, the wing angles backwardly from the blunt cannula.

In accordance with a further feature of the invention, the needle assembly includes a further wing.

In accordance with a further feature of the invention, the needle assembly includes a cylinder concentrically and proximally fixed to the sharp needle and extending distally therefrom. The cylinder slidably holds the blunt cannula. The blunt cannula travels within the cylinder and thereby extends beyond the sharp needle.

In accordance with a further feature of the invention, the cylinder defines a slot. This slot can be longitudinal. In addition, the blunt cannula has a pawl traveling in the slot. The slot can include a barb. The barb locks the pawl when the blunt cannula is extended. By locking the pawl, the barb locks the blunt cannula in a deployed position that guards the needle.

In accordance with a further feature of the invention, the needle assembly includes a syringe connecting longitudinally to the sharp hollow needle cylinder. The syringe includes a cylinder and a plunger traveling longitudinally in the cylinder.

In accordance with a further feature of the invention, the needle assembly includes a further longitudinal cylinder fixed to the blunt cannula. A conventional syringe having a sharp hollow needle and a first cylinder inserts in the needle assembly. The first cylinder travels in the further longitudinal cylinder. The sharp hollow needle extends beyond the blunt cannula when the cylinder is retracted within the further cylinder and withdraws within the blunt cannula when the cylinder is deployed.

In accordance with a further feature of the invention, the further cylinder defines a longitudinal slot and the cylinder includes a pawl traveling in the longitudinal slot.

In accordance with a further feature of the invention, the sharp hollow needle is threaded to connect to a syringe having a complimentary threaded connector.

In accordance with a further feature of the invention, the blunt cannula is threaded to connect to a syringe having a complimentary threaded connector.

In accordance with a further feature of the invention, the sharp hollow needle and the blunt cannula remain water tight under a pressure generated during injection.

Other features that are considered as characteristic for the invention are set forth in the appended claims.

The object of the invention is to provide a needle assembly that prevents accidental sticks with a contaminated needle while allowing access to any drug or multiple dose vials. The needle assembly combines the benefit of using the conventional steel needle, needle shield, and the blunt plastic cannula or needleless needle. The needle assembly has a proximal end and a distal end. The proximal end is near a syringe. The distal end is near the tip of the needle and cannula.

A further object of the invention to provide a female twist lock fitting that joins the proximal end of the device to the male twist lock fitting at the distal end of a syringe. The needle assembly then can encase and permanently bind a conventional steel needle.

Another object of the invention is to provide a needle assembly having wings extending laterally from the female twist lock. The cannula surrounds the needle and is connected to the wings. These wings include a proximal wing element and a distal wing element located bilaterally of the sharp hollow needle. The wings can be unfolded (deployed) so that the cannula extends beyond the tip of the needle. The wings can include locks to prevent them from refolding and exposing the contaminated needle.

In accordance with another feature of the invention, the dimensions of the needle assembly and guard can allow them to be used for intramuscular injections. Intramuscular needles are especially dangerous because they are longer and, therefore, more cumbersome than subdural needles.

Although the invention is illustrated and described herein as embodied in a needle assembly, it is nevertheless not intended to be limited to the details shown, since various modifications and structural changes may be made therein without departing from the spirit of the invention and within the scope and range of equivalents of the claims. An intramuscular needle needs to penetrate the skin and the underlying muscle. Accordingly, intramuscular needles are typically one-and-one-half inches (1 ½") long.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1 is a perspective view of a needle assembly with a needle retracted into a surrounding cannula;

FIG. 2 is a front view of the needle assembly shown in FIG. 1 with the needle retracted into a surrounding cannula;

FIG. 3 is a front view of the syringe in FIG. 1 with the needle deployed;

FIG. 8 is a front view of a needle assembly with a deployed cannula and protected needle;

FIG. 9 is a front view of the needle assembly shown in FIG. 8 with a retracted cannula and extended needle;

FIG. 10 is a bottom view of the needle assembly shown in FIGS. 8 and 9;

FIG. 13 is a cross-sectional view of the wing shown in FIG. 5 taken along line 13—13;

FIG. 14 is a cross-sectional view of an alternate embodiment of the wing shown in FIG. 4 taken along line 12—12; and FIG. 15 is a cross-sectional view of the alternate embodiment of the wing shown in FIG. 5 taken along line 13—13.

DESCRIPTION OF THE PREFERRED EMBODIMENTS

Figure 11:
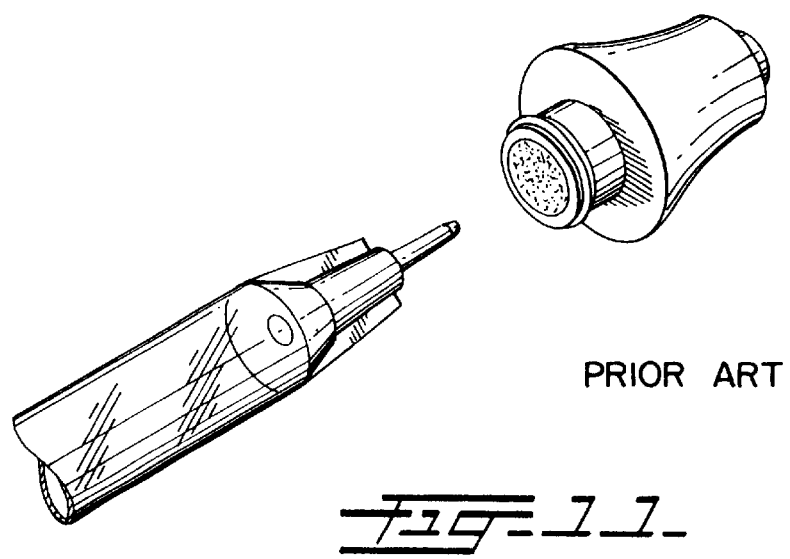
FIG. 11 is a perspective view of a prior art injection port and syringe with a cannula.

Referring now to the figures of the drawing in detail and first, particularly, to FIG. 1 thereof, there is seen a first embodiment of a needle assembly generally marked with reference number 1. The needle assembly 1 includes a syringe similar to the prior art including a second cylinder 5, a plunger 6 travelling in the second cylinder 5, and a needle 2 connected to the second cylinder 5. The second cylinder 5 travels within a first cylinder 4. The first cylinder 4 ends in a blunt cannula 3. The blunt cannula 3 cannot puncture a user's skin. To make an injection with the blunt cannula 3, an injection must be made through an injection port 27 with a pre-made slit 28 (see FIG. 11). To fill the second cylinder 5 from a vile 12 with a rubber septum 13, the cannula 3 is retracted and the needle 2 is extended (see FIG. 3). The needle 2 is sharp and can penetrate the septum 13 of the bottle 14 to withdraw the medicine 14. Once the medicine has been withdrawn into the second cylinder 5 by deploying (extending) the plunger 6, extending the first cylinder 4 relative to the second cylinder 5 deploys the cannula 3. By deploying the cannula 3, the cannula 3 shields and protects the injector (i.e., a nurse or healthcare provider) from the sharp needle 2. The cannula 3 and the sharp hollow needle are concentric. The cannula 3 forms a liquid-tight seal with the needle 2. The liquid-tight seal allows medicine stored in the second cylinder 5 to be injected through the needle 2 and out the deployed cannula 3.

The first (outer) cylinder 4 includes a longitudinal slot 7. A pawl 10 attached to the second cylinder 5 travels in the longitudinal slot 7. The longitudinal slot 7 contains a barb 9. The barb 9 allows the cannula 3 to be deployed but then holds the pawl 10 so that the needle 2 cannot be reextended once the barb 9 locks the pawl 10. FIG. 2 shows the pawl 10 locked by the barb 9 with the cannula 3 extended.

Figures 4, 5:
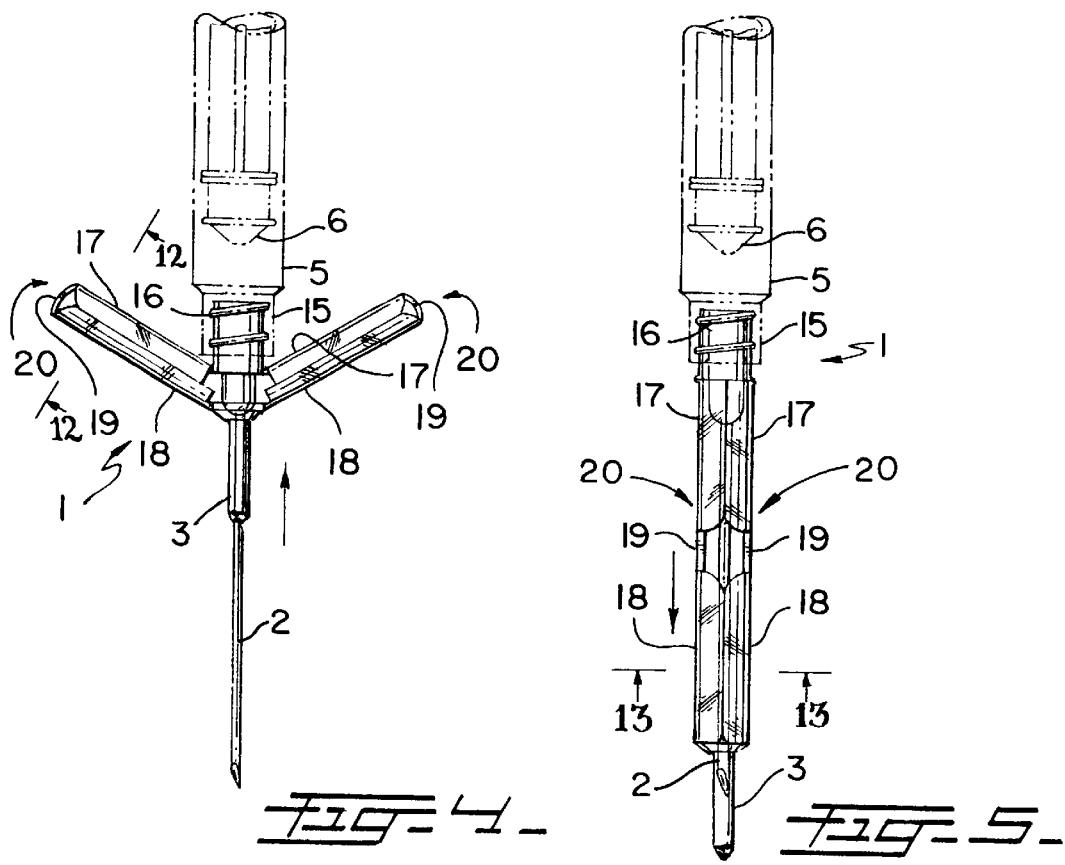
FIG. 4 is a front view of a syringe with a retracted cannula including folded wings.
FIG. 5 is a front view of the syringe shown in FIG. 4 with the cannula deployed by unfolding the wings.

FIGS. 4–5 show a second embodiment. In this embodiment, a prior art syringe is shown in phantom. The syringe includes a cylinder 5 and a plunger 6, and a female socket 15. The needle assembly 1 has a male thread 16 that screws into the female socket 15. A needle 2 is fixed to the male thread 16. A cannula 3 is coaxially mounted around the needle 2 and can slide along its length. Wings 20 connect the cannula 3 and the male thread 16. Each wing has an upper wing element 17 and a lower wing element 18. A hinge 19 connects each upper wing element 17 to its respective lower wing element 18. The wings 20 deploy by unfolding to a straight position shown in FIG. 5. Once deployed, the cannula 3 extends longer than the needle 2. The length of the wings 20 is sized to extend the cannula 3 beyond the tip of the needle 2. Again, the cannula 3 forms a liquid-tight seal with the sharp hollow needle 2. The wings 20 are angled backward (distal from the tip of the needle 2) to prevent the wings 20 from interfering while withdrawing medicine from a vial.

To use the embodiment of the needle assembly 1 shown in FIGS. 4–5, the needle assembly 1 is attached to a prior art syringe. The sharp hollow needle 2 extends beyond the retracted cannula 3 and can pierce the rubber septum of a medicine vial for withdrawal of medicine. The medicine is withdrawn by deploying the plunger 6. Deploying the cannula 3 by unfolding the wings 20 as shown in FIG. 5 protects the still clean needle 2. The cannula 3 is then inserted into an injection port attached to the patient. The medicine is then injected through the injection port into patient by pressing the plunger 6.

Figure 12:
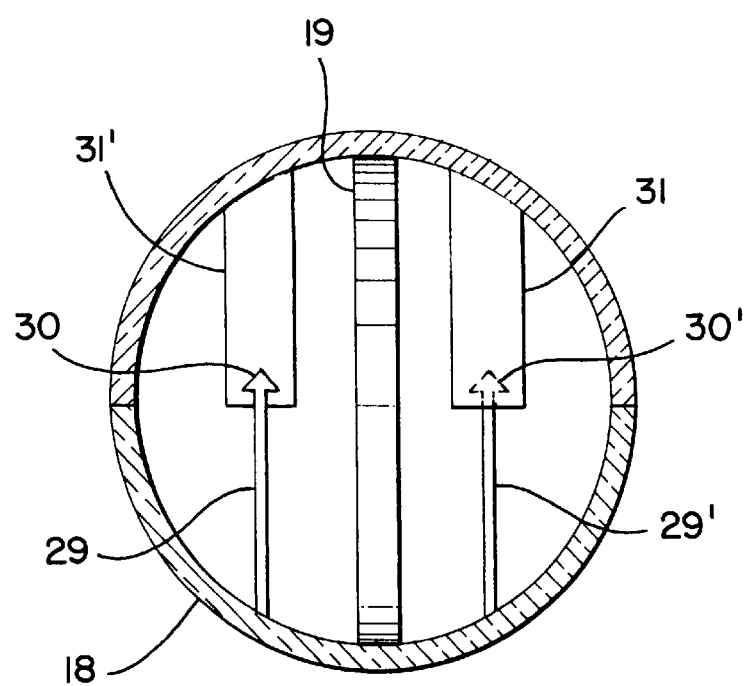
FIG. 12 is a cross-sectional view of the wing shown in FIG. 4 taken along line 12—12.

The wings 20 also can include a lock to irreversibly lock the cannula 3 in its deployed position. FIGS. 12–13 depict a first embodiment of a lock for the wings 20. The lock is formed with a peg 29 and 29' having a barb 30 and 30' that fits into a socket 31. The peg 29 and barb 30 do not lock when the wing 20 is retracted; see FIGS. 4 and 12. FIG. 12 shows that when the wing 20 is folded, the barb 30 of the peg 29 does not insert into the socket 31. In contrast, in FIG. 13, when the wing 20 is unfolded, the barb 30 of the peg 29 inserts into the socket 31 and cannot be removed; this prevents the wing 20 from refolding.

An alternate embodiment of the lock is shown in FIGS. 14–15. In the second embodiment, one of the wing elements 17 or 18 has a peg 29 with a barb 30. The cannula 3 is retracted and the wing 20 is folded in FIGS. 4 and 15. When the cannula 3 is extended beyond the tip of the needle 2 when the wings 20 are unfolded, the peg 29 and the barb 30 lockingly engage the needle 2 and prevent the sharp needle from becoming exposed by preventing the wings 20 from unfolding; see FIGS. 5 an 14.

Figures 6, 7:
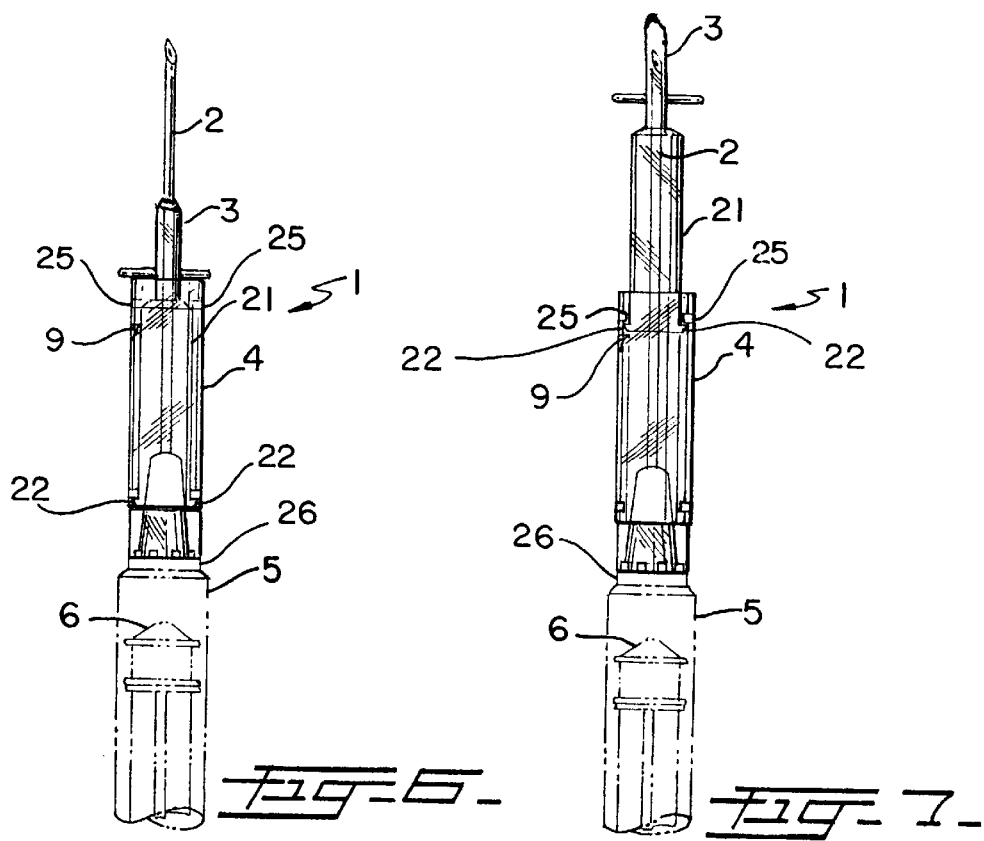
FIG. 6 is a front view of a needle assembly with a retracted cannula and exposed needle.
FIG. 7 is a front view of the needle assembly shown in FIG. 6 with a deployed cannula and protected needle.

FIGS. 6 and 7 show an alternate embodiment of a needle assembly 1. Again, the needle assembly 1 can be attached to a syringe of the prior art shown in phantom. The needle assembly 1 has a male thread 16 that connects to the female socket 15 in the syringe; the male thread 16 and female socket 15 are shown in FIGS. 4–5. A sharp hollow needle 2 is fixed to the male thread 16 and is fluidly connected to the second cylinder 5 of the syringe. The needle assembly has a first cylinder fixed to the male thread 16. Concentrically therewith, a third cylinder 21 is located. The third cylinder 21 deploys and retracts with regard to the first cylinder 4. In this embodiment, the third cylinder 21 retracts within the first cylinder 4. The third cylinder 21 has lateral pawls 22 and the first cylinder has grooves (not shown) in which the pawls 22 travel to guide the third cylinder 21 in relation to the first cylinder 4. The cannula 3 is attached to the end of the third cylinder 21. The cannula 3 is concentric with the needle 2 and surrounds it. FIG. 6 shows how the retracted needle assembly 1 attaches to the second cylinder 5 at the connector 26. The connector 26 can be any standard connector such as a threaded screw on connector. In the retracted position, the needle 2 extends beyond the cannula 3. FIG. 7 shows, the needle assembly 1 in a deployed position. The third cylinder 21 has been extended relative to the first cylinder 4. The third cylinder 21 has pawls 22 that abut the stops 25 of the second cylinder that prevent the third cylinder 21 from extending too far. Barbs 9 can be added to the second cylinder 4 to lock the cannula 3 in the deployed position.

FIGS. 8–10 show an additional embodiment of the needle assembly 1. A prior art syringe is shown having a second cylinder 5, a plunger 6, and a male thread 16. The needle assembly 1 includes a collar 8 that attaches to the male thread 16. A hollow needle 2 is fixed to the collar 8. A first cylinder 4 slides within the collar 8. The cannula 3 is connected to the first cylinder 4. By sliding the cylinder 4 within the collar 8, the cannula can be deployed as in FIG. 8 or retracted as in FIG. 9. When deployed, the cannula 3 extends longer than the needle 2 and barbs 9 irreversibly lock against the collar 8 and prevent the cylinder 4 from retracting. Stops 25 on the cylinder 4 prevent the first cylinder from sliding completely past the collar 8. FIG. 10 is a bottom view of the embodiment shown in FIGS. 8 and 9. The bottom view shows how the cylinder 4 and 5 are arranged with regard to the collar 8.

I claim:

1. A needle assembly comprising:

a sharp hollow needle for penetrating a septum of a vial;

a blunt cannula for injecting into an injection port, said blunt cannula concentrically surrounding said sharp hollow needle, forming a liquid-tight seal with said sharp hollow needle, and retractably extending relative to said sharp hollow needle, whereby said blunt cannula is useable for injecting into an injection port after extending relative to said sharp hollow needle to shield said sharp hollow needle.

2. The needle assembly according to claim 1, including a syringe connected longitudinally to said blunt cannula.

3. The needle assembly according to claim 1, including a wing having an upper wing element and a lower wing element joined by a hinge, said wing fixed proximally to said hollow needle and unfolding at said hinge to extend said blunt cannula beyond said sharp hollow needle.

4. The needle assembly according to claim 3, wherein said wing includes a lock preventing said wing from unfolding once said wing has been unfolded.

5. The needle assembly according to claim 4, wherein said lock includes a peg with a barb on one of said wing elements and a socket on a second of said wing elements, said barb engaging said socket when said wing is unfolded.

6. The needle assembly according to claim 4, wherein said lock includes a peg with a barb on one of said wing elements, said barb engaging said needle when said wing is unfolded.

7. The needle assembly according to claim 3, wherein said wing angles backwardly from said blunt cannula.

8. The needle assembly according to claim 3, including a further wing.

9. The needle assembly according to claim 1, including:

a cylinder concentrically and proximally fixed to said sharp needle and extending distally therefrom, said cylinder slidably holding said blunt cannula, said blunt cannula traveling within said cylinder and thereby extending beyond said sharp needle.

10. The needle assembly according to claim 9, wherein:

said cylinder defines a longitudinal slot; and said blunt cannula has a pawl traveling in said longitudinal slot.

11. The needle assembly according to claim 10, wherein said cylinder defines a latitudinal slot distally connected to said longitudinal slot having a barb, said barb locking said pawl when said blunt cannula is extended.

12. The needle assembly according to claim 1, including a syringe connecting longitudinally to said sharp hollow needle cylinder, said syringe including a cylinder and a plunger traveling longitudinally in said cylinder.

13. The needle assembly according to claim 12, including a further longitudinal cylinder fixed to said blunt cannula, said first cylinder fixed to said sharp hollow needle and traveling in said further longitudinal cylinder, said sharp hollow needle extending beyond said blunt cannula when said cylinder is deployed within said further cylinder and being withdrawn within said blunt cannula when said cylinder is retracted.

14. The needle assembly according to claim 13, wherein said further cylinder defines a longitudinal slot and said cylinder includes a pawl traveling in said longitudinal slot.

15. The needle assembly according to claim 14, wherein said further cylinder defines a latitudinal slot connected distally to said longitudinal slot, said latitudinal slot including a barb locking said pawl when said needle has been withdrawn into said blunt cannula by deploying said cylinder relative to said further cylinder.

16. The needle assembly according to claim 1, wherein said sharp hollow needle is threaded to connect to a syringe having a complimentary threaded connector.

17. The needle assembly according to claim 1, wherein said blunt cannula is threaded to connect to a syringe having a complimentary threaded connector.

18. The needle assembly according to claim 1, wherein said sharp hollow needle and said blunt cannula remain water tight under a pressure generated during injection.

\* \* \* \* \*

UNITED STATES PATENT AND TRADEMARK OFFICE
CERTIFICATE OF CORRECTION

PATENT NO. : 6,685,677 B2  Page 1 of 1
DATED : February 3, 2004
INVENTOR(S) : Christopher H. Green It is certified that error appears in the above-identified patent and that said Letters Patent is hereby corrected as shown below:

Column 7,
Lines 11-20, please delete claim 1 and insert in lieu thereof the following:
-- 1. A needle assembly comprising:

a sharp hollow needle for penetrating a septum of a vial; and a blunt cannula for penetrating an injection port, said blunt cannula concentrically surrounding said sharp hollow needle, forming a liquid-tight seal with said sharp hollow needle, and retractably extending relative to said sharp hollow needle from a first position in which said sharp hollow needle is exposed to a second locked position in which said sharp hollow needle is shielded, whereby said cannula is useable for penetrating an injection port after extending to said locked position to shield said sharp hollow needle. --

Signed and Sealed this

Twenty-fifth Day of May, 2004

JON W. DUDAS
*Acting Director of the United States Patent and Trademark Office*